US008017325B2

(12) United States Patent
Dorai (10) Patent No.: US 8,017,325 B2
(45) Date of Patent: Sep. 13, 2011

(54) SELECTION OF HIGH-PRODUCING CELL LINES

(75) Inventor: Haimanti Dorai, Radnor, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 351 days.

(21) Appl. No.: 12/021,270

(22) Filed: Jan. 28, 2008

(65) Prior Publication Data

US 2009/0191545 A1 Jul. 30, 2009

Related U.S. Application Data

(60) Provisional application No. 60/887,711, filed on Feb. 1, 2007.

(51) Int. Cl.
*G01N 33/53* (2006.01)
*C12N 5/06* (2006.01)
*C12N 15/63* (2006.01)

(52) U.S. Cl. .............................. 435/6; 435/326; 435/455

(58) Field of Classification Search ........................ None
See application file for complete search history.

(56) References Cited

U.S. PATENT DOCUMENTS 7,888,117 B2 2/2011 Dorai et al.
2005/0118652 A1 6/2005 Lee et al.

FOREIGN PATENT DOCUMENTS

EP 0 725 829 B1 8/1996

OTHER PUBLICATIONS

Barnes et al., Biotechnology and Bioengineering, (2007, v.96, pp. 337-348.*
Dorai et al (Hybridoma, 2006, v.25, pp. 1-9.*
Borth J. of Biotechnology, 1999, v.67, pp. 57-66.*
PCT International Search Report dated Oct. 30, 2008.
Supplementary European Search Report dated Apr. 23, 2010.
Aldrich, et al., "EASE Vectors for Rapid Stable Expression of Recombinant Antibodies," Biotechnology Prog., 19: 1433-1438 (2003).
Barnes, et al., "Molecular Analysis of Successful Cell Lines Selection in Transfected GS-NS0 Myeloma Cells," Biotechnology and Bioengineering, 96: 337-348 (2007).
Barnes, et al., "Molecular Definition of Predictive Indicators of Stable Protein Expression in Recombinant NS0 Myeloma Cells," Biotechnology and Bioengineering, 85(2): 115-121 (2004).
Bebbington, et al., "High-Level Expression of a Recombinant Antibody from Myeloma Cells Using a Glutamine Synthetase Gene as an Amplifiable Selectable Marker," Biotechnology, 10: 169-175 (1992).
Brekke, et al., "Therapeutic Antibodies for Human Diseases at the Dawn of the Twenty-First Century," Nature Review, 2: 52-62 (2003).
Deans, et al., "Expression of an immunoglobulin heavy chain gene transfected into lymphocytes," Proceedings of the National Academy of Science USA, 81: 1292-1296 (1984).
Dempsey, et al., "Improved Fermentation Processes for NS0 Cell Lines Expressing Human Antibodies and Glutamine Synthetase," Biotechnology Progress, 19: 175-178 (2003).
Dorai, et al., "Correlation of Heavy and Light Chain mRNA Copy Numbers To Antibody Productivity in Mouse Myeloma Production Cell Lines," Hybridoma, 25(1): 1-9 (2006).
Dorai, et al., "Genome-Wide Analysis of Mouse Myeloma Cell Lines Expressing Therapeutic Antibodies," Biotechnology Progress, 23: 911-920 (2007).
Dorai, et al., "The Effect of Dihydrofolate Reductase-Mediated Gene Amplification on the Expression of Transfected Immunoglobulin Genes," The Journal of Immunology, 139: 4232-4241 (1987).
Figueroa, et al., "Aven and Bcl-$x_L$ Enhance Protection Against Apoptosis for Mammalian Cells Exposed to Various Culture Conditions," Biotechnology and Bioengineering, 85: 589-600 (2004).
Foecking, et al., "Powerful and versatile enhancer-promoter unit for mammalian expression vectors," Gene, 45: 101-105 (1986).
Fouser, et al., "High Level Expression of a Chimeric Anti-Ganglioside GD2 Antibody: Genomic Kappa Sequences Improve Expression in COS and CHO Cells," Bio/Technology, 10: 1121-1127 (1992).
Ganguly, et al., "Mammalian Expression Systems," Gene Cloning and Expression Technologies, Eaton Publishing, p. 115-141 (2002).
Gorfien, et al., "Growth of NS0 Cells in Protein-Free, Chemically Defined Medium," Biotechnology Progress, 16: 682-687 (2000).
Jiang, et al., "Regulation of Recombinant Monoclonal Antibody Production in Chinese Hamster Ovary Cells: A Comparative Study of Gene Copy Number, mRNA Level, and Protein Expression," Biotechnology Progression, 22: 313-318 (2006).
Randall J. Kaufman, "Selection and Coamplification of Heterologous Genes in Mammalian Cells," Methods in Enzymology, 185: 547-566 (1990).
Kaufman, et al., "Improved vectors for stable expression of foreign genes in mammalian cells by use of the untranslated leader sequence from EMC virus," Nucleic Acids Research, 19(16): 4485-4490 (1991).
Knight, et al., "Construction and Initial Characterization of a Mouse-Human Chimeric Anti-TNF Antibody," Molecular Immunology, 30(16): 1443-1453 (1993).
Köhler, et al , "Immunoglobulin chain loss in hybridoma lines," Proceedings of the National Academy of Science USA, 77(4): 2197-2199 (1980).
Kwaks, et al., "Identification of anti-repressor elements that confer high and stable protein production in mammalian cells," Nature Biotechnology, 21: 553-559 (2003).
Lekas, et al., "The Human Cytochrome P450 IAI Is Rapidly Degraded in HepG2 Cells," Archives of Biochemistry and Biophysics, 384(2): 311-318 (2000).
Lee, et al., "A Clone Screening Method Using mRNA Levels to Determine Specific Productivity and Product Quality for Monoclonal Antibodies," Bioetchnology and Bioengineering, 102(4): 1107-1118 (2009).
Lee, et al., "Development of Apoptosis-Resistant Dihydrofolate Reductase-Deficient Chinese Hamster Ovary Cell Line," 2003, 82 (7) : 872-876.
Looney, et al., "High-level expression and characterization of a mouse-human Chimeric CD4 antibody with therapeutic potential," Human Antibody Hybridomas, 3: 191-200 (1992).
Lucas, et al., "High-level production of recombinant proteins in CHO cells using a dicistronic DHFR intron expression vector," Nucleic Acids Research, 24(9): 1774-1784 (1996).

(Continued)

*Primary Examiner* — Michail Belyavskyi
(74) *Attorney, Agent, or Firm* — Kirk Baumeister (57) ABSTRACT

The invention describes a method for screening antibody producing cell lines for selection of high expressing clones.

11 Claims, 6 Drawing Sheets

OTHER PUBLICATIONS

McLean, et al., "Human and murine immunoglobulin expression vector cassettes," Molecular Imunology, 37, 837-845 (2000).

Niwa, et al., "Efficient selection for high-expression transfectants with a novel eukaryotic vector," Gene, 108: 193-200 (1991).

Nwagwu, et al., "Ribonucleic acid synthesis in embryonic chick muscle, rates of synthesis and half-lives of transfer and ribosomal RNA species," Journal of Embryology and Experimental Medicine, 56: 253-267 (1980).

0i, et al , "Immunoglobulin gene expression in transformed lymphoid cells," Proceedings of the National Academy of Science USA, 80: 825-829 (1983).

Page, et al., "High Level Expression of the Humanized Monoclonal Antibody Campath-1H in Chinese Hamster Ovary Cells," Bio/Technology, 9: 64-68 (1991).

F.R. Schmidt, et al., "Recombinant expression systems in the pharmaceutical industry," Applied Microbiology Biotechnology, 65: 363-372 (2004).

Seong, et al , "Enhancement of B-MYB Transcriptional Activity by ZPR9, a Novel Zing Finger Protein," The Journal of Biological Chemistry, 278(11): 9655-9662 (2003).

John J. Trill, "Monoclonal Antibody Expression in Mammalian Cells," Gene Cloning and Expression Technologies, Eaton Publishing, pp. 143-162 (2002).

Tsai, et al., "Nucleic acid capture assay, a new method for direct quantitation of nucleic acids," Nucleic Acids Research, 31(6): e25-e31 (2003).

Florian M Wurm, "Production of recombinant protein therapeutics in cultivated mammalian cells," Nature Biotechnology, 22: 1393-1398 (2004).

Xia, et al., "High levels of protein expression using different mammalian CMV promoters in several cell lines," Protein Expression and Purification, 45: 11-124 (2006).

Yoshikawa, et al., "Amplified Gene Location in Chromosomal CAN Affected Recombinant Protein Production and Stability of Amplified Genes," Biotechnology Progress, 16: 710-715(2000).

* cited by examiner

SELECTION OF HIGH-PRODUCING CELL LINES

CLAIM TO RIGHT OF PRIORITY

This application claims the benefit of U.S. Provisional Application Ser. No. 60/887,711, filed 1 Feb. 2007, the entire contents of which is incorporated herein by reference in its entirety.

FIELD OF THE INVENTION

The invention relates to methods of producing therapeutic proteins derived from immunoglobulin genes such as monoclonal antibodies. The invention relates to methods of producing high expressing host cells lines for the purpose of therapeutic protein manufacture.

BACKGROUND OF THE INVENTION

The market share of biopharmaceuticals is rapidly increasing. Over 1000 new biopharmaceutical products are in the development pipeline globally. The growth of the biopharmaceuticals market is thus driving a need for increased manufacturing capacity. However, the construction of new biomanufacturing facilities is very expensive, ranging from $50 million for a small pilot plant to over $500 million or more for a commercial facility. In addition, it takes over 4 years to bring new facilities on line, as regulatory authorities must validate all aspects of the manufacturing process.

The initial selection of host cell also influences the design of the downstream process and the number of required unit operations, such as number of bioreactor runs. Thus, the efficiency of production of any one product will translate into reduced manufacturing volume or capacity requirement and therefore overall reduced costs. One basic method by which this can be achieved, is by the creation of host cell lines that produce stable molecules and at a high rate of expression.

A number of methods have been used to increase the expression of therapeutic proteins including therapeutic monoclonal antibodies (Abs) in various mammalian cell hosts (reviewed in Wurm, et al. 2004 Nat. Biotechnol. 22, 1393-1398; Ganguly and Jin, 2002 and Trill, 2002). These include: a) the use of strong viral promoters, e.g., human cytomegalovirus promoter (Deans et al., 1984) or cellular promoter e.g., the beta-actin promoter (Niwa et al., 1991); b) the amplification of transfected genes using dihydrofolate reductase (DHFR) gene as an amplifiable marker (Kaufman, 1990) both in DHFR-negative Chinese hamster ovary cell lines (Page and Sydenham, 1991) and in myeloma cell lines (Dorai and Moore, 1987); c) the use of the glutamine synthase selection system (Bebbington et al., 1992); and d) the use of dicistronic vectors where the amplifiable marker is expressed at much lower levels compared to the recombinant protein of interest, and therefore amenable to a high degree of gene amplification and expression (Lucas et al., 1996; Kaufman et al., 1991). In addition, the use of targeted integration of the gene of interest to chromosomal 'hot spots' of expression (Aldrich et al., 2003 and Koduri et al., 2001) and the use of insulator sequences and anti-repressor elements in the expression vector (Zahn-Zabal et al., 2001; Kwacks et al., 2003) have yielded promising results, although their use in therapeutic protein expression is yet to be realized. Due to these and many other improvement efforts, cell lines that express therapeutic proteins with specific productivity as high as 100 picograms/cell/day have been developed (Page and Sydenham, 1991).

In order to increase the worldwide capacity for manufacturing protein products using existing facilities, cell lines with even higher productivity than those that are currently available need to be developed. Methods for screening to select such a cell line would be of utility in expediting the process of developing high expressing cell lines for manufacture of therapeutic proteins.

SUMMARY OF THE INVENTION

One aspect of the invention is a method of for selecting a cell line for production of antibodies comprising the steps of transfecting an antibody encoding gene, comprising at least a heavy chain gene and, optionally, a light chain gene, into two or more suitable mammalian host cells; culturing the transfected host cells; quantitating the mRNA encoded by the antibody gene in the host cells; and selecting the host cell with highest mRNA quantity.

DETAILED DESCRIPTION OF THE INVENTION

Abbreviations

Abs antibodies, polyclonal or monoclonal; CHO Chinese hamster ovary; HC Heavy Chain; LC Light Chain; Mab monoclonal antibody; QPCR Quantitative PCR; MMb Mimetibody; cDNA Complementary DNA; mRNA messenger RNA; GS glutamine synthase; MHX mycophenolic acid, hypoxanthine and xanthine.

Definitions

The term "antibody" is intended to encompass antibodies, digestion fragments, specified portions and variants thereof, including, without limitation, antibody mimetics or comprising portions of antibodies that mimic the structure and/or function of an antibody or specified fragment or portion thereof, including, without limitation, single chain antibodies, single domain antibodies, minibodies, and fragments thereof. Functional fragments include antigen-binding fragments that bind to the target antigen of interest. For example, antibody fragments capable of binding to a target antigen or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the term antibody (see, e.g., Colligan, Immunology, supra). Thus, the term antibody, as used herein also includes antibody fragments either produced by the modification of whole antibodies or synthesized de novo using recombinant DNA methodologies.

By "high producing cell line", "high productivity", and "clone having superior producing levels", or "high expressing" clone is meant an engineered cell line, a transfectoma, or clone thereof which, when growing in conditions comparable to other cells engineered to express an antibody, produce relatively higher concentrations of the antibody in the cell culture medium than other cells similarly grown. Antibody concentration, and therefore production, may be measured by any number of standard or nonstandard methods and be quantitative, e.g. as amount produced per unit volume, or be relative as, e.g., the density of a antibody complex produced in solution and measured by, e.g., nephelometry or in a semisolid medium such as methylcellulose.

"Growth rate" refers to the rate of proliferation of cells. In a culture, the growth rate may be monitored by assessing the density of viable cells per unit volume in the culture at distinct time points. When the growth rate is typically fastest (or highest), the cells are in "log phase" growth due to the abundance of nutrients, including oxygen, energy, and substrates for all cellular components and processes. Growth rate may be expressed in terms of # viable cells/ml/day. Growth rate may also be expressed as "doubling time" or the time that the culture takes for the number of cells per unit volume to double. Therefore, the faster the growth rate, the lower the doubling time value.

"Specific productivity" means the amount of protein product produced by a cell or specific number or cells per unit time. Specific productivity may be expressed as, e.g., $\mu g/10^6/$day or as pg/cell/day. Specific productivity may also be calculated by, e.g. dividing the values for productivity (mg or ug of protein per unit of culture volume) and the viable cell density (cells per unit volume).

By "stability" or "stable clone" is meant that the amount of protein product produced by a cell or specific number or cells per unit time does not appreciably decrease on passaging. That is, upon subcloning and subsequent passaging, the specific productivity of a cell line is maintained at the desired rate.

Description

The importance of the initial selection of a stable, high producing cell line is critical for development of a Master Cell Bank (MCB) for the process of biopharmaceutical manufacturing. Any change in the cell bank during clinical studies requires additional regulatory documentation and experimentation, which leads to increased costs and may delay the supply of material for ongoing clinical trials significantly. The initial selection of host cell also influences the design of the down stream process and the number of required unit operations, such as the number of bioreactor runs, and therefore 'scalability' is important.

In attempts to improve productivity of antibody manufacturing cell lines, we asked whether there was a correlation of either heavy (H) or light (L) chain mRNA transcript levels to Ab productivity (Dorai, et al. 2006. Hybridoma 25: 1-9). A correlation between these parameters would suggest that higher expressing cell lines could be obtained by increasing the H and/or L chain mRNA transcript levels or selecting cell lines having increased H and/or L chain mRNA transcript levels. To determine if such a correlation exists, a large number of recombinant monoclonal Ab producing cell lines were examined. These cell lines were generated after cotransfection of recombinant H and L chain genes of therapeutic antibodies into mouse myeloma host cell lines with the aim of developing cell lines suitable for manufacturing the protein of interest. Total RNA was prepared from exponential cultures of these cell lines and analyzed for H and L chain mRNA copy number using the quantitative PCR (QPCR) method. At the same time, the Ab titer of these cell lines was determined. The results suggest that in most of the cell lines tested, within experimental error, L chain transcript level was more abundant than that of H chain transcript and there was a correlation of H and L chain transcript levels to Ab productivity. However, this correlation was particularly noteworthy for the H chain. These findings imply that transcription of these genes is probably one of the rate-limiting steps in the antibody expression pathway.

In one instance (Dorai, 2006 supra), Ab productivity was examined in primary transfectomas which were produced from transfection of various antibody genes under control of their original endogenous promoters into non-secretors of endogenous immunoglobin (NS0) derived host cell lines present in constructs including gpt gene as a dominant selection marker (using MHX). Sublcones of the primary transfectomas were also examined. The productivity ranged from about 10 ug/ml to over 200 ug/ml for individual cell lines cultured under similar culture conditions. While productivity can be dependent on the differences in the strengths of the corresponding immunoglobulin promoters, subcloning a subset of the primary transfectomas produced cell lines with Ab titers 2 to 7-fold enhanced and other clones in which productivity did not increase or increased only marginally. It was discovered that the increase in antibody titer of the subclones (compared to their primary clones) positively correlated with an increase in Heavy chain and Light chain mRNA levels; higher expressers were associated with approximately $1.0 \times 10^7$ and $1.5 \times 10^7$ copies of Heavy and Light chain per 10 ng of cDNA respectively. Generally, the level of Light chain mRNA was higher compared to the level of Heavy chain in a majority of the cell lines and the difference in their levels was not due to differential stability of the message. For stable cell lines expressing over 100 mg/L Ab in shake-flask cultures, the copy number of L chain ranged from 10 to $20 \times 10^6$ copies per 10 ng cDNA, while that of the H chain ranged from 4 to $10 \times 10^6$ copies per 10 ng cDNA. The findings indicate that Heavy chain mRNA is a superior predictor of cell line productivity than the Light chain mRNA, and Light chain message is generally present in excess quantity to the Heavy Chain message.

In another report (Barnes et al. 2007. Biotechnol Bioengineer 96 (2): 337-348), NS0 myeloma cells transfected with heavy and Light chain antibody genes along with the GS gene were analyzed for the specific mRNA for these genes and the data related to specific productivity of the transfectants. Data was reported for specific productivity of the cultures of individual NS0 transfected by electroporation with a vector encoding for both the heavy and light chains of an anti-CD38 antibody, each under control of separate CMV promoters and GS gene was under control of a SV40 promoter. The correlation coefficient for the relationship between heavy chain percent mRNA expression and specific productivity was $R^2=0.7747$ while that for light chain percent mRNA expression and specific productivity was $R^2=0.4659$ and for GS mRNA copy and specific productivity was $R^2=0.0082$. Thus, this study produced results that indicate the heavy chain mRNA copy number is a better predictor of cell productivity than light chain copy number or selection marker mRNA copy number in a system wherein the antibody genes are under control of a non-native promoter.

This information can be used for predictive identification of stable, high expressing production cell lines with desirable growth rates that are useful for antibody manufacturing purposes. Additionally, individual cells with high levels of Heavy Chain and, optionally, Light Chain transcripts can be selected directly by, e.g., a high throughput RT-PCR screening method, yielding Ab expressing cell lines with high productivity in a greatly reduced time-frame.

The invention relates to methods for selecting a high producing cell line after transfection of the antibody encoding genes into a suitable mammalian host cell. In one embodiment of the method of the invention, one or more host cells are transfected with a gene encoding a antibody heavy chain and a gene encoding an antibody light chain and, optionally, a gene encoding a selectable marker protein, followed by culture of the transfected host cell to form a transfectoma, and after the initiation of antibody production by the host cell, the mRNA coding for the heavy chain is quantitated in the host cells and the host cell with highest mRNA quantity is selected.

In another embodiment, the absolute copy number of heavy chain mRNA copy number is used to select transfectomas for retention. In yet another embodiment, one transfectoma is subcloned and the heavy chain mRNA in the cultured subclones producing antibody is used to select clones for retention.

Thus, a method of screening for high antibody expressing cell lines (high producers) using heavy chain mRNA quantitation can be used in a variety of mammalian host cell line systems and can be used independently or in concert of other parameters, characteristics, or selection criteria.

Host Cells and Selection of High Producing Clones

The host cell capable of producing a protein comprising an immunoglobulin heavy chain can optionally be at least one selected from E. Coli, COS-1, COS-7, HEK293, BHK21, CHO, BSC-1, HepG2, Ag653, SP2/0, NS0, 293, HeLa, myeloma, lymphoma, yeast, insect or plant cells, or any derivative, immortalized or transformed cell thereof.

In the method of the invention the eukaryotic cell is a myeloma cell. Examples of myeloma cell lines useful in the methods of the invention include the SP2/0, NS0 (European Collection of Cell Cultures (ECACC), Salisbury, Wiltshire, UK, ECACC No. 85110503), FO (ATCC CRL-1646), and Ag653 (ATCC CRL-1580) cell lines which were obtained from mice. An example of a myeloma cell line obtained from humans and useful in the methods of the invention is the U266 cell line (ATTC CRL-TIB-196). The C463A myeloma cell line is also useful in the methods of the invention and is an example of an SP2/0 derived cell line capable of growing in chemically defined media. Those skilled in the art will recognize other useful myeloma cell lines.

In the method of the invention the eukaryotic cell can also be selected from the group consisting of SP2/0, C463A, and CHO cells. Each of these cell types have the common properties of being suitable for in vitro culture and having the ability to express peptide chains at high levels.

The development of a manufacturing process for a recombinant protein in mammalian cells has been well established. Initially, vectors comprising the recombinant gene, or in the case of antibodies or other heterodimeric proteins, recombinant genes for both the heavy and the light chain, along with the necessary transcriptional regulatory elements is transferred to the cells. At the same time, an additional gene that confers to recipient cells a selective advantage may be transferred. Calcium phosphate transfection, electroporation, lipofection and biolistic- and polymer-mediated gene transfer are routinely used to affect transfer of the gene comprising vectors into the host cells to create transfectomas.

In the presence of the selection agent, which is applied after gene transfer, only those cells that express the selector gene survive. Genes for selection are commonly those which encode an enzyme essential to produce a metabolite in a pathway critical for cell proliferation such as dihydrofolate reductase (DHFR) and glutamine synthase (GS). In both cases, selection occurs in the absence of the appropriate metabolite (hypoxantine and thymidine, in the case of DHFR, glutamine in the case of GS), preventing growth of nontransformed cells. Another form of selection gene is one that codes for a protein that will confer resistance to the cells against the presence of a toxic substance. An example of such a system is the MHX, where selection medium contains mycophenolic acid, hypoxanthine and xanthine and the marker gene is GPT (guanosine phosphoribosyl transferase). In general, for efficient expression of the recombinant protein, it is not important whether the biopharmaceutical-encoding gene(s) and selector genes are on the same plasmid or not. Following selection, which may be by a process of limited dilution cloning of the transfectomas, survivors are transferred as single cells to a second cultivation vessel, and the cultures are expanded to produce clonal populations (clones). Eventually, individual clones are evaluated for recombinant protein expression, with the highest producers being retained for further cultivation and analysis. From these candidates, one cell line with the appropriate growth and productivity characteristics is chosen for process development and production of the recombinant protein. A cultivation process is then established that is determined by the production needs.

The method of the invention for evaluating or screening the transfected host cells, the transfectomas, having survived any chemical selection process as described comprises the use of a method to quantitate the mRNA coding for one or more of the antibody chains present during culture of the cells and during a period time that antibody protein coded for by the transfected genes is secreted into the culture medium. Following transfection of a therapeutic protein into a host cell, a set of primary transfectomas, may optionally first be screened and categorized according to the amount of secreted antibody concentration in the culture medium (titer) or superior growth properties such as high viability. In a typical cell line development effort, approximately 600-1000 primary transfectomas are screened for antibody titer and about 50 transfectomas are selected for further study of their clonal progeny. For example, clones may be grown as a 50 ml culture of in a 125 ml shake-flask by seeding $2 \times 10^5$ cells/ml, incubating at 37° C. with shaking for 7d or until the viability drops more than 10%, whichever is earlier. At that point the Ab concentration in culture fluid can be measure using a nephelometer and a binding reagent such as an Ab specific antigen or a rabbit anti-human polyclonal antibody. The nephelometer detects immunochemical complexes by sample forward light scattering.

According to the method of the invention, the antibody chain mRNA screen is applied to the tranfectomas. The heavy chain mRNA screen according to the method of the invention is a method of quantitating transfected gene message, heavy and light chain mRNA, in the cells producing and secreting antibody into the culture media. In one embodiment of the method, the method to detect the transfected gene mRNA is a rapid high-throughput quantitative PCR method. In one method of practicing the invention, the protocols and procedures described in the examples provided herein below may be employed for the screen. In one embodiment of the method of the invention, the transfected gene mRNA measurement is applied to those transfectomas showing superior antibody titer as compared to all transfectomas.

Having described the method of screening of transfectomas by transfected antibody gene mRNA and their progeny, it will be apparent that the number of candidate clone lines to be tested in bioreactors will be greatly reduced along with the effort, man-hours, real time, and bioreactor space that must be expended to develop a suitable clone of an engineered host cell line suitable for therapeutic antibody production.

Antibodies

Antibody classes (also known as isotypes) are IgE, IgD, IgA, IgM, and IgG). Antibodies are specialized immunoglobulin molecules that comprise a basic heterotetrameric glycoprotein of about 150,000 daltons, composed of two identical light (L) chains and two identical heavy (H) chains. An antibody of the IgG class comprises two heavy chains and two light chains. Each chain has a constant region (C) and a variable region (V). Each chain is organized into a series of domains. The light chains have two domains, corresponding to the CL region and to the VL region. The heavy chains have four domains, one corresponding to the VH region and three domains (C1, C2 and C3) in the C region. Each heavy and light chain also has regularly spaced intrachain disulfide bridges. In human IgG antibodies, the constant domain of the light chain is aligned with the first constant domain of the heavy chain, and the light chain variable domain is aligned with the variable domain of the heavy chain. Particular amino acid residues are believed to form a noncovalent interface between the light and heavy chain variable domains (Clothia et al., *J. Mol. Biol.* 186, 651-66, 1985); Novotny and Haber, *Proc. Natl. Acad. Sci. USA* 82 4592-4596 (1985). The two heavy (H) chains are inter-connected by disulphide bonds at an interdomain region in the heavy chains known as the hinge. In addition, antibodies may be further typed or classified into subclasses based on biophysical and biological properties, e.g., IgG1, IgG2, IgG3, and IgG4, conferred by sequence similarities particularly those in the constant domains.

An antibody can include or be derived from any mammal, such as but not limited to a human, a mouse, a rabbit, a rat, a rodent, a primate, or any combination thereof and includes isolated human, primate, rodent, mammalian, chimeric, humanized and/or CDR-grafted antibodies, immunoglobulins, cleavage products and other specified portions and variants thereof. Antibodies can be prepared in several ways well known in the art. In one aspect, the antibodies are conveniently obtained from hybridomas prepared by immunizing a mouse with a target protein, variant, or fragment thereof. The antibodies can thus be obtained using any of the hybridoma techniques well known in the art, see, e.g., Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference. Genes encoding the H and L chains of an antibody of interest can then be isolated from hybridoma cell lines by techniques well known to those skilled in the art.

Methods of Quantitating mRNA

Specific sequences in RNA preparations can be detected by blotting and hybridization analysis using techniques very similar to those originally developed for DNA (Southern blotting) as described in, e.g., Current Protocols in Molecular Biology 2004. John Wiley & Sons, Inc. Brown et al. "Analysis of RNA by Northern and Slot Blot Hybridization" UNIT 4.9. Fractionated RNA is transferred from an agarose gel to a membrane support (northern blotting); unfractionated RNA is immobilized by slot or dot blotting. The resulting blots are studied by hybridization analysis with labeled DNA or RNA probes. RNA slot blotting is a simple technique that allows immobilization of unfractionated RNA on a nylon or nitrocellulose membrane. Hybridization analysis is then carried out to determine the relative abundance of target mRNA sequences in the blotted samples. The technique is based on the DNA dot- and slot-blotting procedure, the main difference being the way in which the samples are denatured prior to immobilization.

RNase protection can be used to determine the amount of a specific RNA in a mixture. Hybridization of a RNA to a labeled, single-stranded probe protects it from digestion by a single-strand specific nucleasne. The size of the protected region can be determined by gel electrophoresis.

Reverse transcriptase PCR (RT-PCR) is a modification of the polymerase chain reaction in which a DNA copy is first made from RNA by reverse transcriptase, then the reaction is subjected to PCR. To use for quantitating RNA, must have an internal control. The mRNA for ribosomal 18S RNA is often used as the internal standard.

The quantitation of one or multiple species of mRNA may also be achieved using technologies, such as microarrays, macroarrays, gene chips, serial analysis of gene expression (SAGE), RT-PCR, and EST sequencing. These technologies produce data which may be helpful in monitoring a set of genes which may have a known relationship of one to another or genes whose expression levels have collectively been identified to relate to a single process such as antibody expression. These data are often collected in a high-throughput environment, providing individual expression profiles that are unique to individual conditions or treatments, tissues, or disease states, or clones. Interpretation of the results requires an understanding both of the variety of techniques for analyzing data and of the computer tools available for storing and visualizing them (Current Protocols in Bioinformatics. 2003 John Wiley & Sons, Inc. Grewal et al. "Analysis of Expression Data: An Overview." Unit 7.1).

Specific types of sensitive high-throughput methods of detecting specific mRNA have been described such as the bDNA assay (Urdea, et al. 1987. Gene 61: 253-264; Kern et al. 1996. J. Clin. Microbiol. 34: 3196-3202; Collins, et al. Nucleic Acids Res. 25: 2979-2984) also available from Chiron Diagnostic as the "Quantigene bDNA signal amplification kit" and the nucleic acid capture assay (NACA) (Tsai et al., 2003, Nucleic Acids Research. 31(6): e25-31).

As practiced in the method of the invention, the method of quantitation of the heavy chain antibody gene mRNA in the engineered cell line, transfectoma, or clone thereof, is may be performed by a variety of methods described and known in the art. The method of the invention relates to the use of the heavy chain antibody gene mRNA to select cells which will be high producing cell lines for antibody manufacturing purposes.

The present invention is further described with reference to the following examples. These examples are merely to illustrate aspects of the present invention and are not intended as limitations of this invention.

Example 1

Development of Myeloma Production Cell Lines

Figure 1:
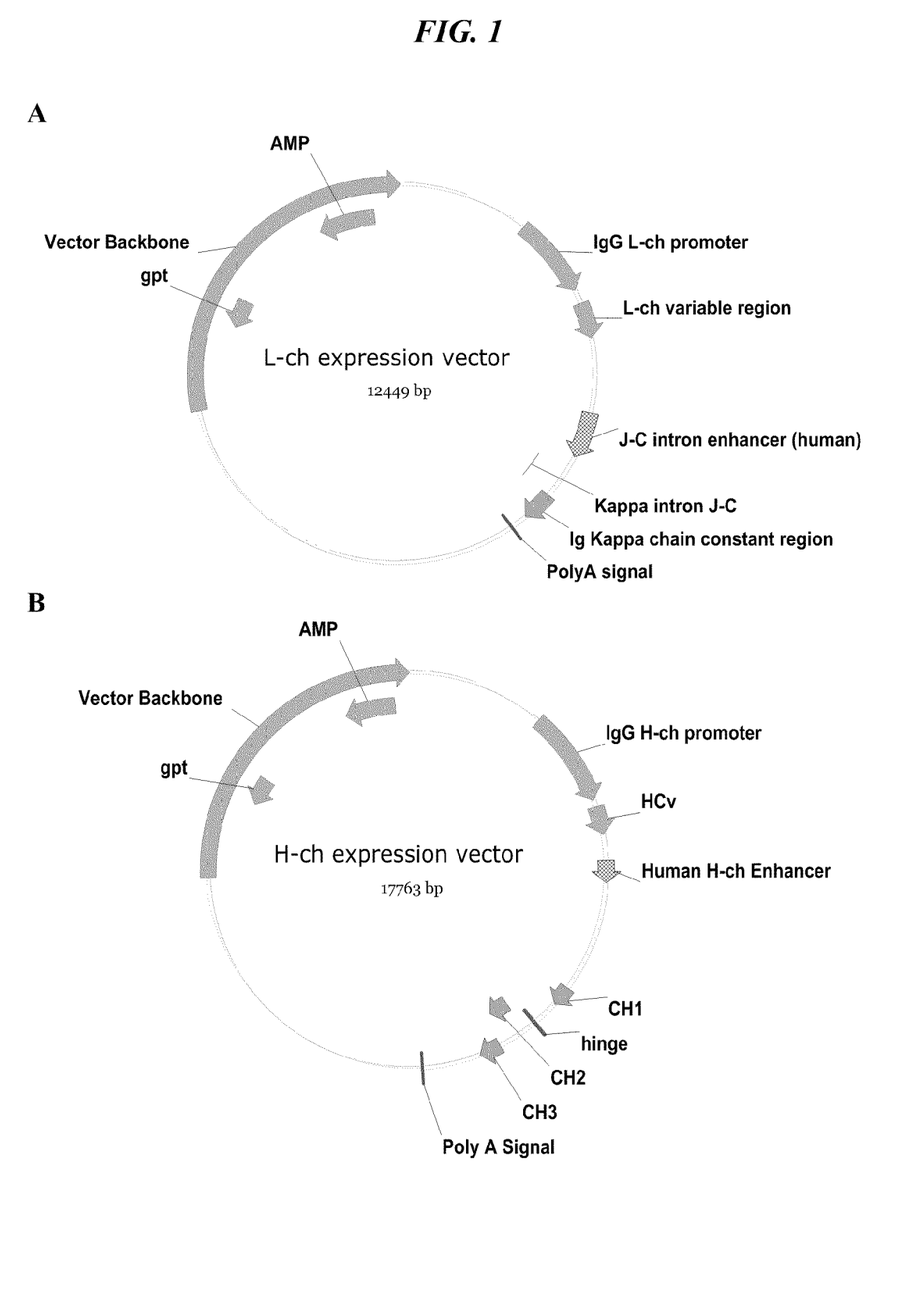
FIG. 1 shows schematics of the expression constructs for heavy and light chain expression: A) Light chain expression vector (12.4 kb) and B) Heavy chain expression vector (17.8 kb).

FIG. 1 shows typical expression constructs encoding mouse/human chimeric H and L chain Ab genes used for developing the production cell lines used in this study. The chimeric Abs were constructed by cloning the mouse H and L chain variable regions (along with their contiguous immunoglobulin promoters) upstream of the constant regions of human Kappa L chain and IgG1H chain, respectively. The human immunoglobulin enhancers of both H and L chains, located between the J and C regions were included in each of the constructs. Mycophenolic acid resistance marker (gpt gene) was present in both constructs as the dominant selection marker.

For developing a production cell line, H and L chain constructs were cotransfected into the mouse myeloma host cell lines, Sp2/0 or CD-Sp2/0 (chemically defined medium adapted Sp2/0) or AgX653. A large number of MHX ((Mycophenolic acid (0.5 mg/L), Hypoxanthine (2.5 mg/L) and Xanthine (50 mg/L)) resistant clones were screened for Ab productivity and a primary clone (transfectoma) was selected for multiple rounds of subcloning. The process of subcloning was terminated when no further improvement in product titer was achievable. Table I lists the primary transfectomas and their subclones that were selected for this study. Ab titer of each cell line, obtained from seven-day shake flask culture, is included in Table 1. Intermediate clones that were generated during the process of production cell line development, where available, are listed in Table 2. In these cases, the cell line chosen to determine the fold-increase in titer and H and L chain transcript levels are in bold.

As shown in Table 1, there was considerable difference in the Ab titer among the primary transfectomas. For example, the cell line C18 expressed only 11.3±1.8 mg/L in comparison to the cell line C128B, which expressed 158.6±13.7 mg/L under similar culture conditions. This difference can be attributed, in part, to the differences in the strengths of the corresponding immunoglobulin promoters. Upon subcloning, a subset of the primary transfectomas with Ab titers 2 to 7-fold enhanced was discovered, while other clones did not increase their titers or increased them marginally (Table 1). While the lack of increase in titer for primary transfectomas with high Ab titers is understandable, (e.g., C128B, 158.6±13.7 mg/L), it is not clear why a primary transfectoma like C18, with very low titer, showed no significant increase in Ab titer upon subcloning (C62, 21.0±3.9 mg/L).

In order to find a predictor of clonal Ab expression level, 30 antibody expressing cell lines with variable antibody expression levels were analyzed for Heavy and Light chain mRNA expression levels. Each cell line was thawed and cultured either in IMDM (Invitrogen) supplemented with 5% heat inactivated fetal bovine serum (Intergen), 6 mM glutamine and MHX (all from Sigma) (IMDM+5% FBS) or CD-Hybridoma medium (Invitrogen) supplemented with 6 mM glutamine and MHX (CD-Hyb) for three passages in shaker flasks. Approximately $1 \times 10^7$ cells were harvested at the exponential growth phase and total RNA was prepared by using an RNAeasy kit (Qiagen). RNA was quantitated by spectrophotometry and its quality was determined using a Lab-on a-chip 2100 Bioanalyzer (Agilent). Two micrograms of the total RNA were used for cDNA preparation using a cDNA synthesis kit (Applied Biosystems) and oligo dT as primer. Antibody titer of 7-day shake flask culture was estimated by nephelometry (Beckman Array Protein System) using an anti-human Ab as the detection agent (Jackson Immunoresearch).

Exponential cultures of C175A, 175-53, 175-88 and C175H cell lines all expressing Ab # 1, and C168A, C168D, C168E and C168J cell lines all expressing Ab # 3, were harvested for isolation of total RNA, retaining an aliquot for further incubation for seven days to determine Ab titer in spent medium. cDNA from these RNA samples were used to determine copy number of H and L chain transcripts. H and L chain expression plasmid DNAs (FIG. 1) of known concentration were used to generate standard curves.

Exponential cultures of C116A and C116E cell lines, expressing Antibody # 5, and C2.320 and C466D cell lines expressing Antibody # 7, were harvested for isolation of total RNA, retaining an aliquot for further incubation for seven days to determine Ab titer in spent medium and treated as described above.

The H and L chain mRNA copy number was determined by the QPCR method, using the Applied Biosystems 7000 instrument. The primers and Taqman probes were designed from the human Kappa constant region and human gamma-1 constant region using the Primer Express software program (Applied Biosystems). The sequence of the various primers and Taqman probes are shown below:

TABLE 1

Fold-increase in Ab titer and H/L chain transcripts in selected cell lines.

| Antibody Number | Host Cell Line | Primary Transfectoma | Subclone | Fold Increase (Ab Titer)[a] | Fold Increase (H/L Transcripts)[a] |
|---|---|---|---|---|---|
| 1 | Sp2/0 | C175A (36.3 ± 1.2)[b] | C175H (114.1 ± 1.3) | 3.1 | 2/2.4 |
| 2 | CD-Sp2/0 | 2C4 (30.5 ± 0.3) | C743B (110) | 3.6 | 2.5/2.1 |
| 3 | Sp2/0 | C168A (6.2 ± 1.4) | C168D (45.6 ± 0.7) | 7.3 | 1.8/5.1 |
| 3 | CD-Sp2/0 | JL2 (27.4 ± 0.6) | C893C (83) | 3 | 2.7/2.8 |
| 4 | Sp2/0 | C128B (158.6 ± 111.7) | C128D (160 ± 13.7) | none | None |
| 5 | Sp2/0 | C116A (6.8 ± 0.1) | C116E (12.4 ± 2.3) | 1.8 | None |
| 6 | Sp2/0 | C18 (11.3 ± 1.8) | C62 (21 ± 3.9) | 1.8 | None |
| 7 | Ag8x653 | C2.320 (6.7 ± 0.5) | C466D (15.1 ± 3.4) | 1.8 | None |
| 8 | Sp2/0 | C505A (16) | C505D (31.5) | 1.9 | 2.1/2.4 |

[a] Fold increase in titer and H/L chain transcripts were determined in the subclone as compared to the corresponding primary transfectomas, using copy number data of Table 2.
[b] Ab titers are given in parenthesis.

Light Chain Probe/Primers:

```
Forward:    5' CCT GAC GCT GAG CAA AGC A              (SEQ ID NO: 1)

Reverse:    5' CAG GCC CTG ATG GGT GAC T              (SEQ ID NO: 2)

qPCR probe: 5' ACT ACG AGA AAC ACA AAG TCT ACG CCT GCG (SEQ ID NO: 3)
```

Heavy Chain Probe/Primers:

```
Forward:    5' TGT CCT ACA GTC CTC AGG ACT CTA CTC    (SEQ ID NO: 4)

Reverse:    5' TGA TTC ACG TTG CAG ATG TAG GT         (SEQ ID NO: 5)

qPCR probe: 5' CTC AGC AGC GTG GTG ACC GTG C          (SEQ ID NO: 6)
```

In some experiments, primers and probe sets (Applied Biosystems) for glyceraldehydes-3-phosphate dehydrogenase (GAPDH) were used to normalize sample-to-sample variations. The fluorescent label for GAPDH was VIC and for H and L chain probes, it was FAM (6-carboxy Fluoroscein). In all cases, the fluorescent quencher dye was TAMRA (Tetramethyl-Rhodmine). Each QPCR reaction contained 10 nanograms of cDNA, 100 nM qPCR primer, 200 nM each of forward and reverse primers, 2×PCR master mix (Applied Biosystems), in a total volume of 50 μl. PCR reactions were denatured by an initial incubation at 90° C. for 10 min, followed by incubation at 90° C. for 0.15 sec and 60° C. for 45 sec. The last two steps were repeated 40 cycles.

An alternate method of determination of the copy numbers of H and L chain, the RNAase protection assay, was performed in selected cell lines using a kit purchased from Ambion.

H and L chain expression constructs (FIG. 1) of known amounts were used to generate the respective copy number standard curves. Using these standard curves, the copy numbers of the H and L chain transcripts for each cell line were determined (Table 2). As it has been demonstrated that these cell lines have only a single H and L chain mRNA species (Looney et al., 1992 and Knight et al., 1993), the level of H chain and L chain mRNAs measured by QPCR in the present study truly reflects the level of full length H chain and L chain transcripts. The data presented in Table 2 suggest that the increase in antibody titer of the subclones (compared to their primary clones) was partly due to an increase in Heavy chain and Light chain mRNA levels; higher expressers were associated with approximately $1.0 \times 10^7$ and $1.5 \times 10^7$ copies of Heavy and Light chain per 10 ng of cDNA, respectively. Generally, the level of Light chain mRNA was higher compared to the level of Heavy chain in a majority of the cell lines and the difference in their levels was not due to their differential stability. The data generated from all the cell lines tested in this study suggested that there was a correlation of Light and Heavy chain transcript levels to antibody productivity, coefficient of correlation being 0.59 for Light Chain and 0.81 for Heavy chain.

TABLE 2

Heavy and Light Chain transcript levels (×10⁶ copies in 10 ng cDNA) in all cell lines used in this study.

| Ab No. (Host) | Cell Line | L Chain | H Chain | Titer |
|---|---|---|---|---|
| 1 (Sp2/0) | C175A | 3.8 ± 0.6 | 1.8 ± 0.2 | 36.27 ± 1.2 |
| | 175-13 | 3.1 ± 0.6 | 1.9 ± 0.3 | 37.53 ± 7.9 |
| | 175-53 | 5.8 ± 0.8 | 2.1 ± 0.2 | 38.86 ± 0.6 |
| | 175-2 | 9.8 ± 0.9 | 3.2 ± 0.4 | 51.75 ± 1.7 |
| | 175-88 | 7 ± 1.0 | 4 ± 0.4 | 90.65 ± 1.5 |
| | C175G | 4.3 ± 0.1 | 2.5 ± 0.2 | 68.04 ± 2.2 |
| | C175H | 9.4 ± 1.3 | 3.6 ± 0.4 | 114.13 ± 1.3 |
| 2 (CD-Sp2/0) | 2c4 | 7.4 ± 1.0 | 2.9 ± 0.2 | 30.52 ± 0.3 |
| | C743B | 13.1 ± 0.7 | 6.6 ± 0.3 | 110.0 |
| | C744B | 17.2 ± 1.1 | 6.9 ± 0.2 | 95.0 |
| 2 (AgX653) | C379b | 48.6 ± 8.8 | 13.3 ± 0.3 | 216.9 ± 9.2 |
| 3 (Sp2/0) | C168A | 2.9 ± 0.2 | 2 ± 0.1 | 6.22 ± 1.4 |
| | C168J | 8.2 ± 0.8 | 2.5 ± 0.3 | 14.615 ± 1.7 |
| | C168E | 19.5 ± 0.8 | 3 ± 0.3 | 34.5 ± 3.9 |
| | C168D | 15.3 ± 1.5 | 3.6 ± 0.3 | 45.57 ± 0.7 |
| 3 (CD-Sp2/0) | jl2 | 2.2 ± 0.1 | 0.6 ± 0.1 | 27.4 ± 0.6 |
| | C893A | 12.4 ± 1.5 | 2.1 ± 0.5 | 64.3 ± 3.5 |
| | C893C | 7 ± 1.7 | 1 ± 0.4 | 83.0 |
| 4 (Sp2/0) | C128B | 13.1 ± 1.0 | 9.7 ± 0.5 | 160 ± 11.7 |
| | C128D | 14.3 ± 2.3 | 10.1 ± 1.0 | 158.6 ± 13.7 |
| 5 (Sp2/0) | C116A | 0.5 ± 0.1 | 1.7 ± 0.1 | 6.79 ± 0.1 |
| | C116E | 1.5 ± 0.1 | 1.4 ± 0.1 | 12.42 ± 2.3 |
| 6 (Sp2/0) | C18 | 1.5 ± 0.0 | 1.3 ± 0.1 | 11.27 ± 1.8 |
| | C62 | 1.1 ± 0.1 | 0.8 ± 0.1 | 21.01 ± 3.9 |
| 7 (AgX653) | C2.320 | 4.6 ± 1.0 | 2.9 ± 0.3 | 6.7 ± 0.5 |
| | C466D | 3.2 ± 0.0 | 2.9 ± 0.7 | 15.15 ± 3.4 |
| 7 (CD-Sp2/0) | C524A | 10.3 ± 0.7 | 6 ± 0.2 | 104.0 |
| | C526A | 8.4 ± 1.0 | 5.6 ± 0.0 | 94.0 |
| 8 (Sp2/0) | C505A | 5.1 ± 0.2 | 3.1 ± 0.5 | 16.0 |
| | C505D | 11.9 ± 0.7 | 6.1 ± 0.5 | 31.5 |

Figure 2:
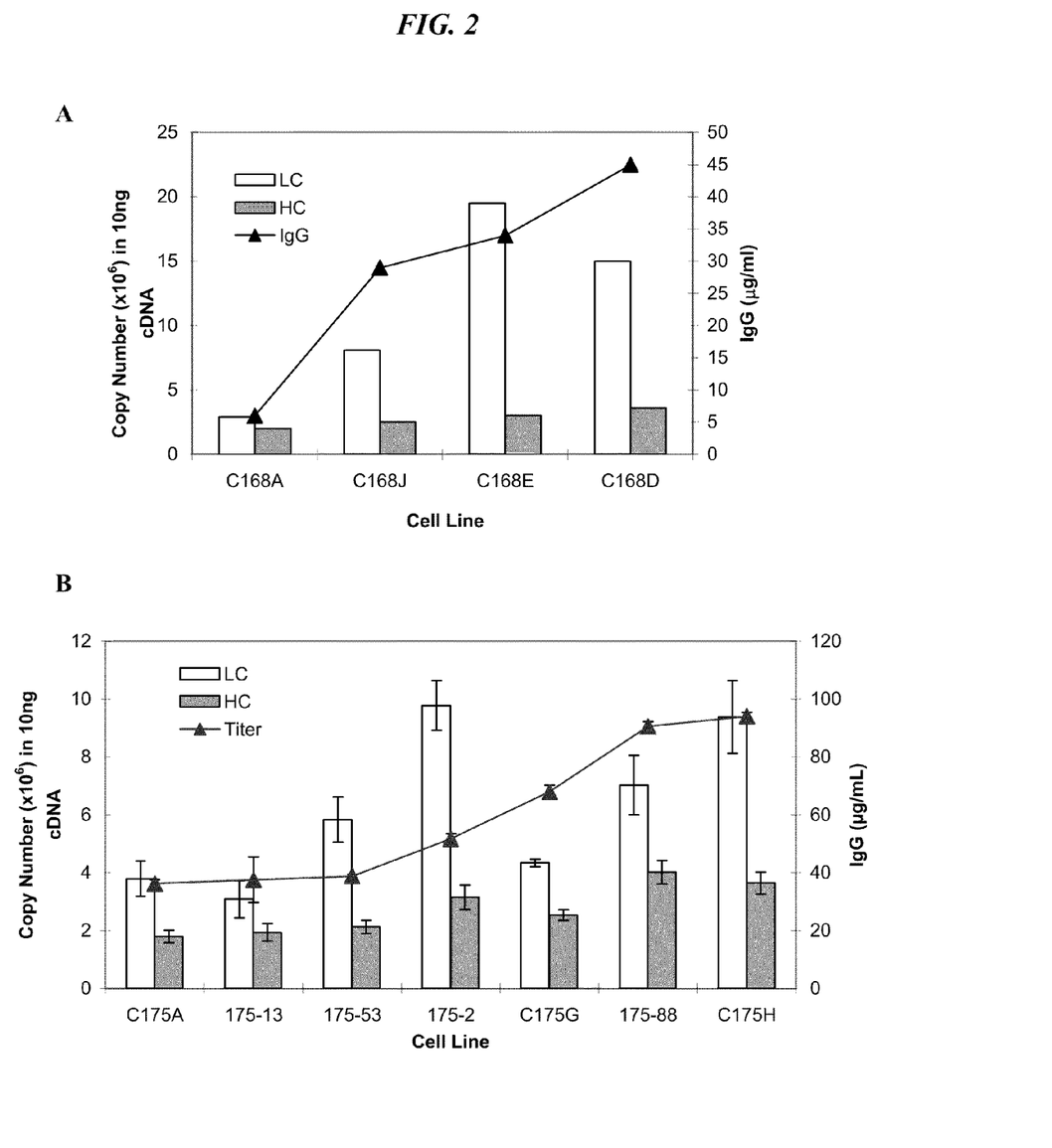
FIG. 2 shows the relationship between antibody titer and copy number of Light and Heavy chain transcripts for cell lines expressing Antibody # 3 (A) and Antibody # 1 (B) in Sp2/0.
Figure 3:
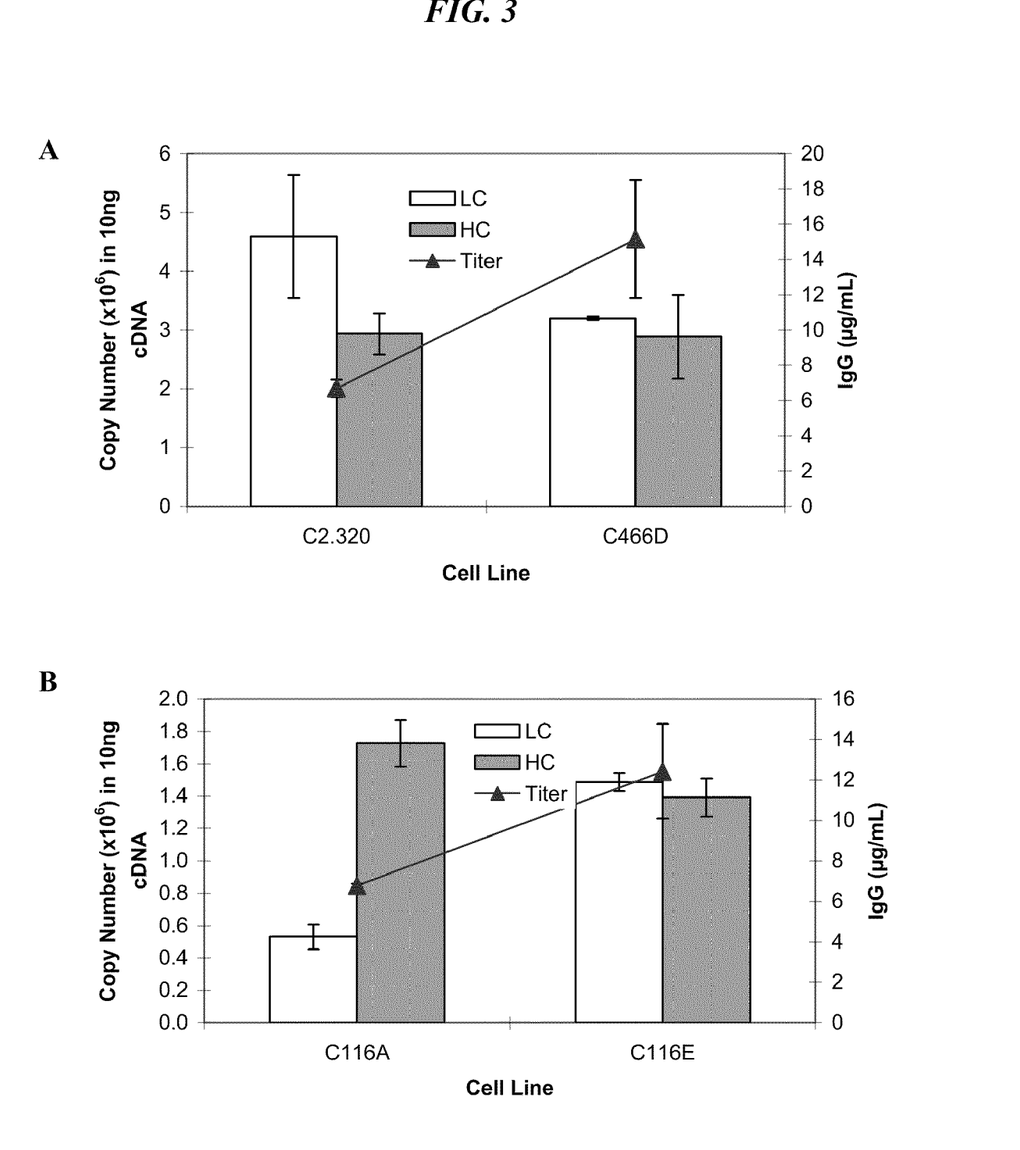
FIG. 3 shows the relationship between antibody titer and copy number of Light and Heavy chain transcripts for cell lines expressing Antibody # 5 (A) and Antibody # 7 (B) in Sp2/0.

In summary, FIG. 2 and Table 1 show examples of Ab expressing cell lines where subcloning of the primary transfectomas led to significant improvements in Ab productivity with a concomitant increase in the copy numbers of the H and L chain transcripts. For example, in the case of Ab # 3 (FIG. 2A), the levels of H and L chain mRNAs increased by 1.8 fold and 5.1 fold, respectively when the primary transfectoma and its subclones were compared. When the titers were analyzed, the subclone C 168D produced about seven-fold more Ab compared to the primary transfectoma C 168A. In all the cell lines in this set, the L chain transcript was more abundant than that of the H chain (as much as 6.5-fold more abundant in one of the higher expressing cell line, C168E).

In the case of Ab # 1 (FIG. 2B), titer increased up to 3.1-fold in the final subclone, C175H when compared to that of the primary transfectoma, C175A whereas the level of H chain and L chain transcripts increased by a factor 2 and 2.4, respectively. As seen for Ab # 3 producing cell lines, the L chain transcripts were more abundant than that of H-chain transcripts for all the cell lines of this set, (up to 3.1-fold more abundant in one of the intermediate cell lines, 175-2).

Figure 4A:
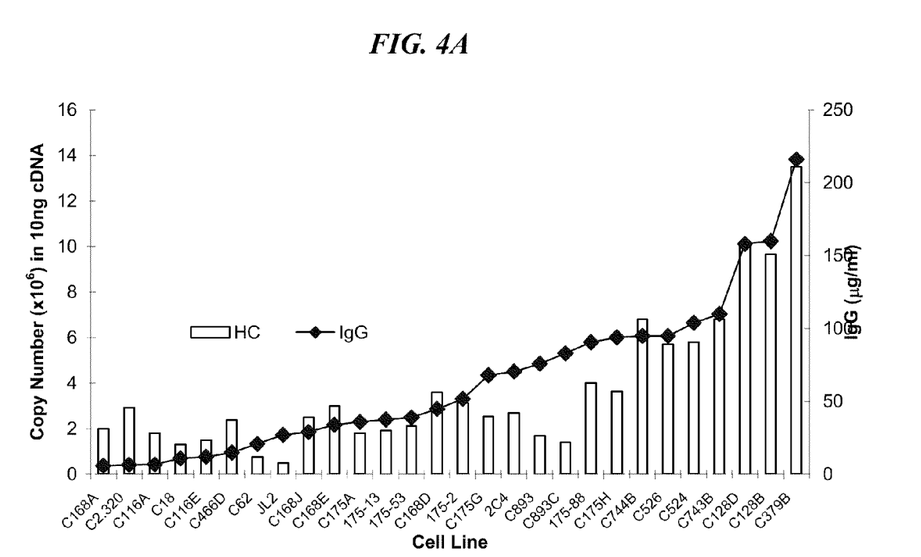
FIG. 4 shows the relationship between antibody titer and copy number of Heavy chain (A) and Light chain (B) transcripts for cell lines examined. Standard deviations for titer and copy number determinations of most cell lines are noted in Table 2.
Figure 4B:
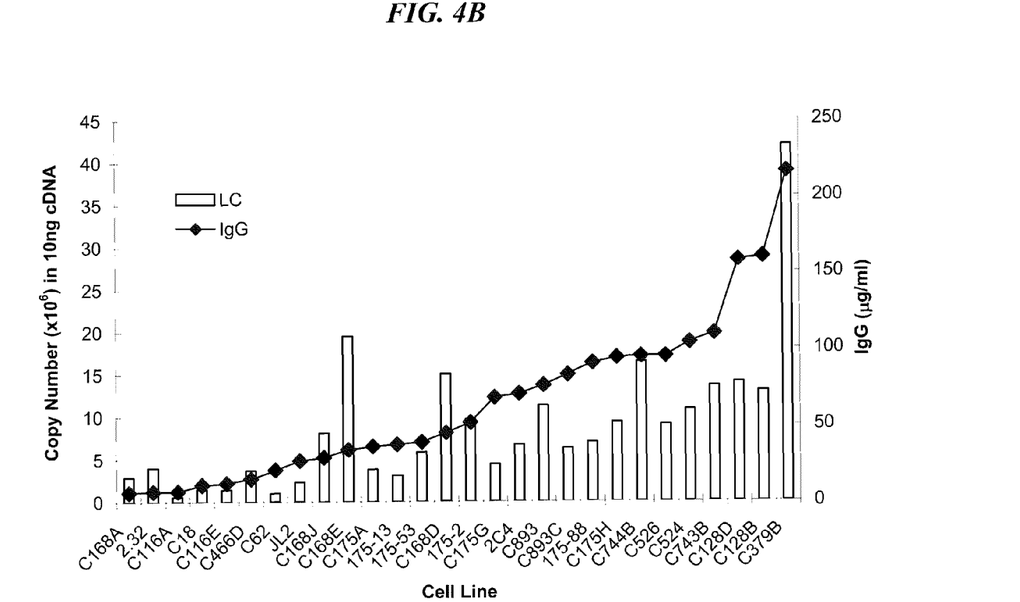
Figure 5:
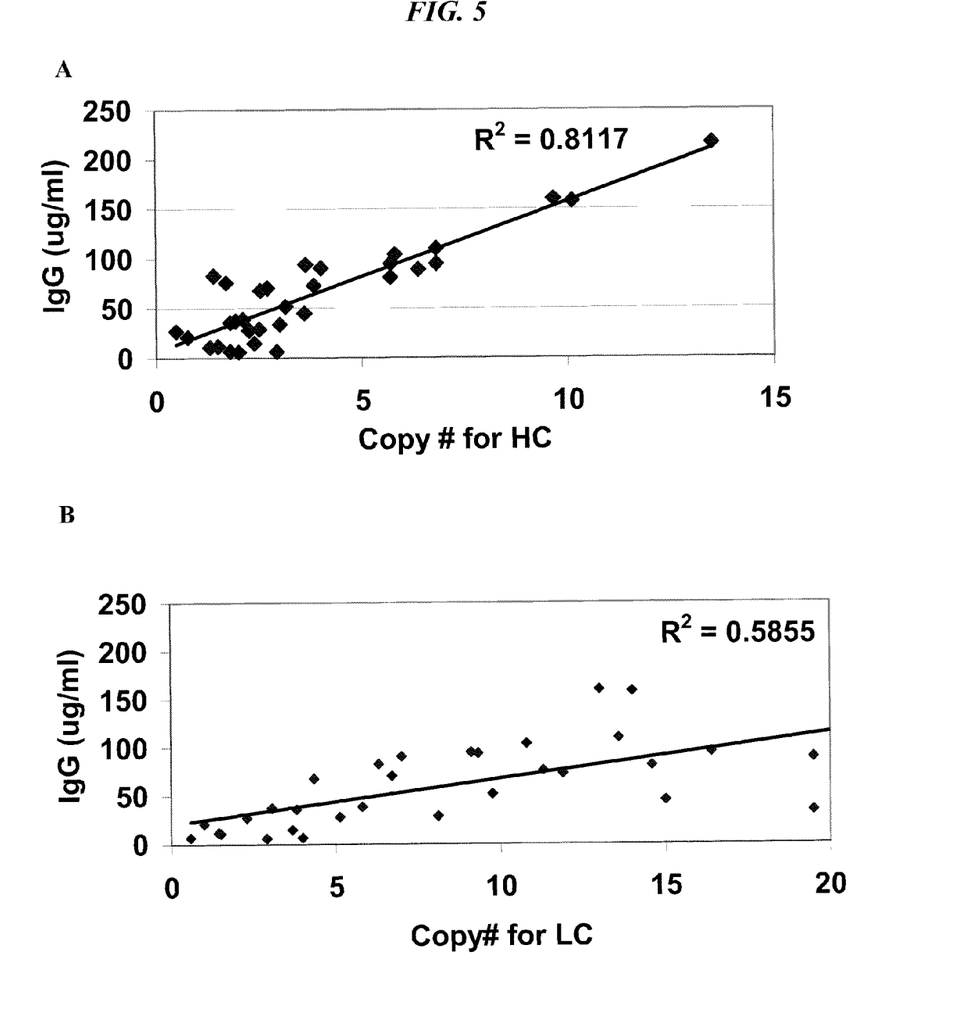
FIG. 5 shows the correlation between antibody Heavy chain (A) and Light chain mRNA (B) to Ab productivity.

When all the cell lines are graded in order of Ab productivity (FIG. 4 and Table 2), we find that generally, the L chain is significantly more abundant than H chain and there is a correlation of H and L chain transcripts to Ab productivity. FIG. 5 (plotting the data from table 2) shows the coefficient of correlation for L chain is 0.59 while it is 0.81 for that of H chain.

Example 2

Stability of H and L Chain Transcripts

The cell line C168J was selected as a representative cell line to compare stability of H chain and L chain mRNAs, as it had the highest ratio of L chain to H chain transcript levels. This cell line was cultured in growth medium containing 5 μg/ml Actinomycin D (Sigma) for a period of 48 hours. At the indicated time points, (Table 2), $5 \times 10^6$ cells were removed to determine the amount of the H and L chain transcripts. The highly stable 18S RNA and GAPDH mRNA (half-life of 67 and 24 hours, respectively (Lekas et al., 2000 and Nwagwu and Nana, 1980)) were used as controls. The reagents used for the estimation of 18S RNA level by QPCR were purchased from Applied Biosystems.

In order to determine if the differential level of H and L chain mRNA is due to their differential stability, half-lives of these two transcripts were compared to that of the housekeeping gene transcripts, GAPDH and 18S RNA which are known to be comparatively more stable (Lekas et al., 2000 and Nwagwu and Nana, 1980). The C168J cell line was grown in the presence and absence of Actinomycin-D for 48 hours to inhibit nascent mRNA synthesis, and the level of each of the four transcripts in the cell samples harvested at the indicated time points (see Table III) was measured by QPCR as described in Example 1.

As summarized in Table 3, the stability of L chain transcript was found to be similar to that of H chain transcript and GAPDH transcript. This demonstrates that the abundance of L chain transcript in C168J was not due the result of its differential stability compared to that of H chain transcript.

TABLE 3

Fold reduction of H and L chain transcripts in C168J cell line over time, following administration of Actinomycin-D.

| Hours | Heavy Chain | Light Chain | GAPDH | 18S Ribosomal |
| --- | --- | --- | --- | --- |
| 0 | 1.00 | 1.00 | 1.00 | 1.00 |
| 3 | 1.14 | 1.03 | 1.02 | 1.48 |
| 6 | 1.60 | 1.88 | 1.37 | 1.56 |
| 8 | 2.81 | 2.76 | 2.66 | 1.10 |
| 10 | 3.56 | 3.10 | 3.99 | 1.18 |
| 12 | 6.01 | 5.43 | 5.46 | 1.06 |
| 24 | 10.0 | 5.41 | 11.7 | 4.46 |

The invention claimed is:

1. A method for selecting a cell line for production of antibodies comprising the steps of:
   a. transfecting an antibody encoding gene, comprising at least a heavy chain gene and, optionally, a light chain gene, into two or more suitable mammalian host cells;
   b. culturing the transfected host cells;
   c. quantitating the mRNA encoded by the antibody heavy chain gene in the host cells; and
   d. selecting the host cell with highest heavy chain gene mRNA quantity.

2. The method of claim 1 further comprising the step of determining heavy chain gene mRNA copy number per cell and selecting those cells with a specified copy number.

3. The method of claim 1 or 2 wherein the transfection step further comprises transfection of a selectable marker gene.

4. The method of claim 3 wherein the selectable marker is DHFR, GPT, or GS.

5. The method of claim 3 wherein the culturing step comprises subcloning in selection medium.

6. The method of claim 5 wherein the growth rate and productivity of the selected host cell is determined as a selection criteria.

7. The method of claims 1 wherein the heavy chain mRNA is determined using quantitative PCR.

8. The method of claim 7 wherein the quantitative PCR uses the oligonucleotides having the sequences set forth in SEQ ID NOs: 4-6.

9. The method of claim 2 wherein the heavy chain mRNA codes for a heavy chain selected from the group consisting of IgA, IgG1, IgG2, IgG3, IgG4, IgD, IgE, and IgM.

10. The method of claim 1 wherein the antibody gene is under the control of a promoter selected from the group consisting of an endogenous antibody gene promoter and a CMV promoter.

11. The method of claim 6 further comprising the step of selecting the most stable clone.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Homo sapiens

<400> SEQUENCE: 1
cctgacgctg agcaaagca                                           19

<210> SEQ ID NO 2
<211> LENGTH: 19
<212> TYPE: DNA
<213> ORGANISM: Homo sapiens

<400> SEQUENCE: 2
caggccctga tgggtgact                                           19

<210> SEQ ID NO 3
<211> LENGTH: 30
<212> TYPE: DNA
<213> ORGANISM: Homo Sapiens

<400> SEQUENCE: 3
actacgagaa acacaaagtc tacgcctgcg                               30

<210> SEQ ID NO 4
<211> LENGTH: 27
<212> TYPE: DNA
<213> ORGANISM: Homo sapiens

<400> SEQUENCE: 4
tgtcctacag tcctcaggac tctactc                                  27

```
<210> SEQ ID NO 5
<211> LENGTH: 23
<212> TYPE: DNA
<213> ORGANISM: Homo sapiens

<400> SEQUENCE: 5
tgattcacgt tgcagatgta ggt                                          23

<210> SEQ ID NO 6
<211> LENGTH: 22
<212> TYPE: DNA
<213> ORGANISM: Homo sapiens

<400> SEQUENCE: 6
ctcagcagcg tggtgaccgt gc                                           22
```